United States Patent [19]

Thomson

[11] 4,412,818

[45] Nov. 1, 1983

[54] METHOD FOR SPLINTING ANIMAL TEETH

[75] Inventor: Adam R. Thomson, Edinburgh, Scotland

[73] Assignee: Ewesplint Limited, Edinburgh, Scotland

[21] Appl. No.: 304,628

[22] Filed: Sep. 22, 1981

[30] Foreign Application Priority Data

Sep. 25, 1980 [GB] United Kingdom ............... 8030938

[51] Int. Cl.³ .............................................. A61D 5/00
[52] U.S. Cl. ....................................................... 433/1
[58] Field of Search .................... 433/1, 6, 9, 10, 19, 433/24, 215, 229, 180; 128/89 A; 54/7, 8, 9; 119/1, 134

[56] References Cited

U.S. PATENT DOCUMENTS

| | | | |
|---|---|---|---|
| 3,348,311 | 10/1967 | Weissman | 433/215 |
| 3,437,545 | 1/1970 | Weissman | 433/215 |
| 3,892,035 | 7/1975 | Hall et al. | 433/1 |
| 3,932,940 | 1/1976 | Andren | 433/9 |
| 4,253,828 | 3/1981 | Coles et al. | 433/6 |

Primary Examiner—John J. Wilson
Attorney, Agent, or Firm—Richard D. Weber

[57] ABSTRACT

The economic value of an animal (e.g. a sheep) is enhanced by bonding the incisor teeth together in a group, when the teeth are fully matured, but before trauma of the teeth has occurred, with an apertured brace which is bonded to the group of teeth by means of a hardened bonding composition to leave the incisal edges of the group of teeth exposed. The invention also relates to a splint for stabilizing animal teeth to reduce the risk of trauma.

4 Claims, 4 Drawing Figures

METHOD FOR SPLINTING ANIMAL TEETH

TECHNICAL FIELD

This invention relates to a splint for stabilising a group of teeth in the jaw of any animal having an isolated group of teeth. The invention finds particular application in stabilising the incisor teeth of a sheep.

A complete set of incisor teeth is of vital importance to a sheep since during cropping, the grass is torn by being gripped between the incisal edges of the teeth in the lower jaw and a fibrous pad on the upper jaw. If the lower teeth become broken or lost by trauma during cropping, the animal cannot crop as much food with each bite and will become weakened. When one or more teeth is/are missing the condition is described as "broken mouth" and a broken mouthed sheep is either discarded to lusher pastures or sent for slaughter at an early age reducing, in the case of breeding sheep, its otherwise useful breeding life.

Breeding ewes can expect to provide a useful fertile life of at least four years from the date on which they acquire their full set of mature incisor teeth and trauma to this set of teeth at any time during that four year period can represent a significant financial loss, since ewes are more effective in breeding towards the end of their fertile period than at the beginning.

There is therefore a need for a simple method of stabilising the teeth in an animal such as a sheep to reduce the occurrence of broken mouth and to improve the economics of breeding such animals.

BACKGROUND ART

It has been proposed in U.K. Patent Specification No. 1185047 to fit a prosthetic device over the incisor teeth of a sheep, the device being in the form of an arcuate cap which is secured over the group of teeth either before or after injury to the jaw of the sheep. The cap can be fixed in place in a number of different ways included among which is cementing. However, the cap employed provides a new incisal surface since it completely covers the upper edges of the capped teeth, or extends above such upper edges.

In practice, the incisal edges of the incisor teeth of the sheep are not normally collinear, the somewhat irregular pattern of the incisal edges being reflected by a corresponding pattern in the fibrous pad of the upper jaw. When the complete set of incisor teeth are capped to provide a new incisal edge for the lower jaw, this will, in general, not correspond to the naturally formed pattern on the fibrous pad and accordingly until the fibrous pad has accommodated itself to the incisal edge of the cap; the cropping efficiency of the animal can be impaired.

This invention seeks to avoid the disadvantages of the known device while retaining the advantages of reducing the occurrence of broken mouth in sheep and obviating the need for premature culling of animals by virtue of broken dentition(s).

DISCLOSURE OF THE INVENTION

According to one aspect of the present invention a method of stabilising the teeth in an isolated group of teeth in an animal jaw comprises embracing the group with an apertured brace and a layer of a hardenable bonding composition to leave the incisal edges of the teeth projecting beyond the brace, and allowing the bonding composition to harden and secure the brace around the group.

Desirably, the apertured brace is made of a suitable alloy (e.g. stainless steel) and should be large enough to provide adequate bracing strength to the group of teeth but not so large that it obscures the incisal edges, damages the lower jaw or interferences with the cropping action of the animal. Preferably the thickness of alloy in the brace is such that it can be deformed without undue difficulty by the person fitting the brace to the animal. Suitable plastics materials are contemplated as an alternative to alloy for the apertured brace.

Desirably the external surface of the brace is well polished and the internal surface (e.g. the surface confronting the teeth) is roughened to provide a stronger bond with the bonding composition.

Desirably the labial surface of the brace from top to bottom is somewhat curved and the height of the brace is greater in the centre of the group of teeth than at either end. The lingual surface of the brace will normally be of considerably reduced height compared to the central region of the labial surface.

The bonding composition can be one of the known dental filling materials but particularly preferred materials are catalytically hardenable resins.

According to a further aspect of the invention, a splint for stabilising an isolated group of teeth in the jaw of an animal comprises an apertured brace dimensioned to embrace the group of teeth adjacent to the gums but to leave the incisal edges of the teeth projecting beyond the brace, the surface of the brace confronting the teeth being adapted to co-act with a hardenable bonding composition to ensure that the brace is permanently secured around said group of teeth.

It will be appreciated that since the incisal edges of the teeth are left proud of the brace, the invention secures the advantage over the known prior art of leaving the natural occlusion between teeth and fibrous pad unaffected.

During normal use, the teeth will wear until eventually they become flush with the upper edge of the brace and further wear will then be reduced by the presence of the brace. However, since wear to this point has occurred naturally, there will have been a continual modification of the shape of the fibrous pad to ensure that there is no interruption in normal cropping procedure when this level of wear is attained.

By putting the brace around the incisor teeth of a sheep as soon as those teeth are fully mature, the individual teeth can be stabilised into a massively strong group which will resist the trauma which is common to sheep during cropping throughout their useful life.

The economics of the method of the invention are fully compatible with the economics of sheep breeding and are expected to produce considerable financial advantages in the long term.

BRIEF DESCRIPTION OF DRAWINGS

The invention will now be described by way of example, with reference to the accompanying drawings, in which.

DESCRIPTION OF PREFERRED EMBODIMENTS

Figure 1:
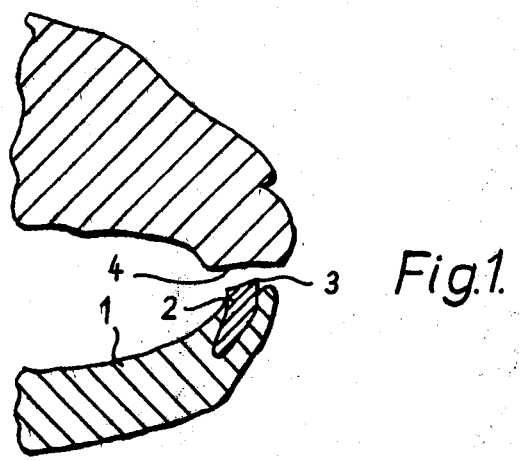
FIG. 1 shows a schematic section of part of the jaws of a sheep.
Figure 2:
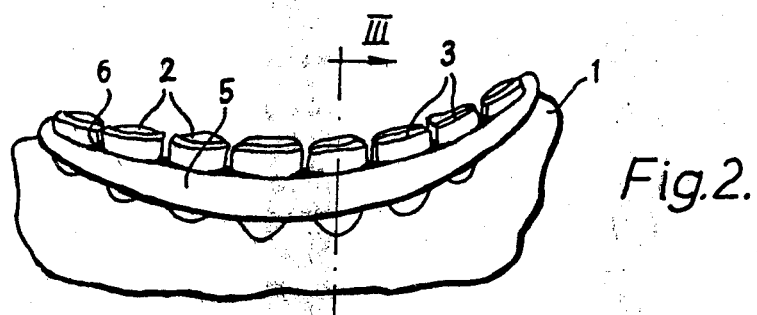
FIG. 2, shows a front view of the incisor teeth of a sheep fitted with a first embodiment of brace in accordance with the method of the invention.

Referring to FIG. 1 the lower jaw 1 of the sheep contains eight incisor teeth 2, the incisal edges 3 of which cooperate with a fibrous pad 4 during cropping. To stabilise the teeth 2 in accordance with the method of the invention they are embraced by an apertured brace 5 secured in place around the group of teeth 2 by a set acrylic resin composition 6. The brace 5 is manufactured of stainless steel and has a maximum thickness of some 3 to 4 millimeters. A considerable excess of composition 6 is employed when fitting the brace 5 around the teeth 2 so that the composition flows between the teeth, completely fills the gaps left between the brace and the teeth on both labial and lingual sides and provides some excess above and below the brace so that this can be removed prior to hardening. In this way it is ensured that the brace is securely bonded in place.

Figure 3:
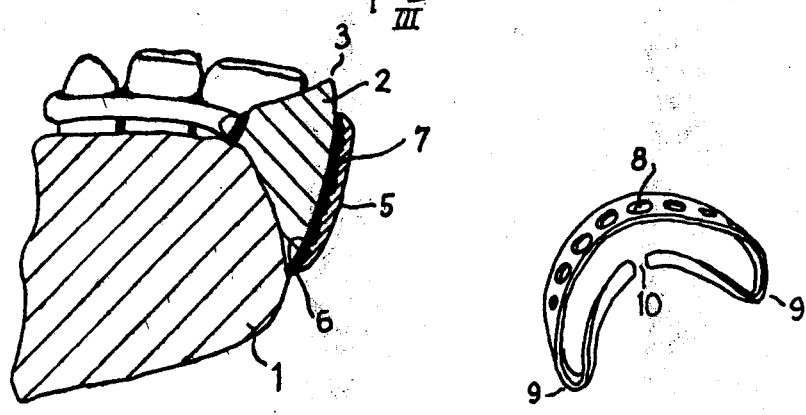
FIG. 3 is a section on the line III—III in FIG. 2.

To improve the degree of securement, the internal surface of the brace (e.g. the surface confronting the teeth) is roughened in some suitable way (as shown at 7 in FIG. 3).

The preferred acrylic resin is based on methyl methacrylate and is applied as a relatively viscous mix and converts to a hard plastics mass in approximately 30 seconds. This time allows for the excess resin to be smoothed off the brace and removed from the incisal edges 3 of the teeth to leave these edges unaffected by the addition of the brace. The mouth can be kept closed while the resin sets.

In place of stainless steel, the brace 5 can be constructed from a chrome cobalt alloy, an aluminium bronze alloy or suitably hard aluminium. Plastics material can also be used for manufacturing the brace.

Figure 4:
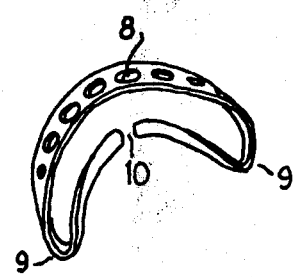
FIG. 4 is a perspective view of a second embodiment.

To improve the bonding effect, holes can be formed in the labial surface through which holes the resin can flow to key the brace more securely to the group of teeth 2, and FIG. 4 shows a form of brace with such holes (marked 8).

The splint shown in FIG. 4 is fabricated by bending a strip of 1 mm thick stainless steel some 11–12 cm long into the shape shown. The maximum height of the labial surface is some 6 mm, tapering to 2 mm at the outer ends 9 thereof. The gap 10 between the ends on the lingual surface of the brace will vary somewhat when the brace is deformed by the fitter to fit around the incisor teeth of a particular sheep. Over the lingual surface, the strip lies so that an edge thereof confronts the teeth.

As an alternative to forming holes in a strip of sheet material, the brace can be fabricated from a strip of meshlike material (e.g. of metal or plastics).

If desired, the cement and/or the brace can include a composition having medicinal or therapeutic applications which composition (e.g. of trace elements) leaches out slowly after the brace has been fitted in place.

What is claimed is:

1. A method of stabilizing the teeth of an isolated group of teeth in the jaw of a ruminant which comprises embracing the group with an apertured brace and a layer of a rapidly hardenable bonding composition to leave the incisal edges of the teeth projecting beyond the brace, and allowing the bonding composition to harden and secure the group within the aperture of the brace.

2. A method as claimed in claim 1, in which the brace is made of a deformable metal alloy and the thickness of alloy in the brace is such that it can be manually deformed without undue difficulty to closely surround the group of teeth by a person fitting the brace to the animal.

3. A method as claimed in claim 1 or claim 2, in which the bonding material is a catalytically hardenable resin.

4. A method of enhancing the economic value of a sheep which comprises bonding the incisor teeth of the sheep, when the teeth are fully matured but before trauma of the teeth has occurred, into a group with an apertured brace bonded to the teeth by means of a hardened bonding composition while leaving the incisal edges of the group of teeth exposed to contact the fibrous pad of the upper jaw of the sheep.

* * * * *